US008998800B2

(12) United States Patent
Masaki (10) Patent No.: US 8,998,800 B2
(45) Date of Patent: Apr. 7, 2015

(54) ENDOSCOPE (71) Applicant: Olympus Medical Systems Corp., Tokyo (JP)

(72) Inventor: Yutaka Masaki, Mitaka (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/904,679

(22) Filed: May 29, 2013

(65) Prior Publication Data

US 2013/0303855 A1 Nov. 14, 2013

Related U.S. Application Data (63) Continuation of application No. PCT/JP2012/063472, filed on May 25, 2012.

(30) Foreign Application Priority Data

Jun. 14, 2011 (JP) ................................. 2011-132586

(51) Int. Cl.
*A61B 1/00* (2006.01)
*A61B 1/005* (2006.01)
(Continued)

(52) U.S. Cl.
CPC .......... *A61B 1/0052* (2013.01); *G02B 23/2476* (2013.01); *A61B 1/0016* (2013.01)

(58) Field of Classification Search
CPC .................................................... A61B 1/0052
USPC ......... 600/146, 147, 150, 104, 114, 148, 149; 604/510; 348/45
See application file for complete search history.

(56) References Cited

U.S. PATENT DOCUMENTS 4,721,099 A * 1/1988 Chikama ........................ 600/152
5,007,406 A * 4/1991 Takahashi et al. ............. 600/119

FOREIGN PATENT DOCUMENTS

JP 07-184845 A 7/1995
JP 08-187222 A 7/1996
(Continued)

OTHER PUBLICATIONS

Machine Translation of Noritomo JP 2010-000201, Jan. 7, 2010; translation from Espacenet.com.*

(Continued)

*Primary Examiner* — Anhtuan T Nguyen
*Assistant Examiner* — Timothy J Neal
(74) *Attorney, Agent, or Firm* — Scully, Scott, Murphy & Presser, PC (57) ABSTRACT An endoscope has a bending portion operation apparatus at an operation portion, the bending portion operation apparatus being for bending and operating a bending portion, and the bending portion operation apparatus includes a dial for bending operation which bends the bending portion by pivoting about a shaft, a portion of the dial for bending operation provided at the operation portion being protruded at a position where the dial for bending operation is operated with a thumb grasping the operation portion, and an auxiliary dial for bending operation which has a meshing portion meshing with the dial for bending operation and a protruding portion protruding at a position where the auxiliary dial for bending operation is operable with a finger other than the thumb, an operation input entered at the protruding portion with the finger other than the thumb being transmitted to the bending operation dial via the meshing portion.

7 Claims, 8 Drawing Sheets (51) Int. Cl.
*G02B 23/24* (2006.01)
*A61B 1/04* (2006.01)

(56) References Cited

FOREIGN PATENT DOCUMENTS

| JP | 2005-160791 A | 6/2005 |
| JP | 2005-245545 A | 9/2005 |
| JP | 2007-222671 A | 9/2007 |
| JP | 2010-000201 A | 1/2010 |

OTHER PUBLICATIONS

International Search Report dated Aug. 28, 2012 issued in PCT/JP2012/063472.

* cited by examiner

ENDOSCOPE

CROSS REFERENCE TO RELATED APPLICATION

This application is a continuation application of PCT/JP2012/063472 filed on May 25, 2012 and claims benefit of Japanese Application No. 2011-132586 filed in Japan on Jun. 14, 2011, the entire contents of which are incorporated herein by this reference.

BACKGROUND OF THE INVENTION

1. Field of the Invention

The present invention relates to an endoscope for bending and operating a bending portion provided at an insertion portion with a bending portion operation apparatus provided at an operation portion.

2. Description of the Related Art

In recent years, endoscopes capable of making observations or providing various therapeutic treatments by inserting an elongated insertion portion into a body have been utilized in a medical field. A bending portion which is configured, for example, to bend in upward, downward, leftward, and rightward directions is provided on an insertion portion distal end side of an endoscope having a flexible insertion portion.

The bending portion is configured to bend in the upward, downward, leftward, and rightward directions by, for example, pivotably linking a plurality of bending pieces. Bending wires that are pulling members whose distal ends are fixed to the bending pieces constituting the bending portion are inserted in and extend through the insertion portion. A bending portion operation apparatus for pulling the bending wires is provided at an operation portion located at a proximal end of the insertion portion. The bending portion operation apparatus includes, for example, a pulley, and proximal ends of the bending wires are fixed to the pulley.

According to the configuration, the bending portion is operated to bend in a surgeon's intended direction by the surgeon who operates the bending portion operation apparatus with fingers of one hand grasping the operation portion and pulling a desired one of the bending wires. As a result, the surgeon can easily perform, for example, insertion of the insertion portion of the endoscope into a site to be examined. The surgeon also can easily perform observation by directing an observation optical system disposed at a distal end portion of the insertion portion toward a target direction.

Examples of the bending portion operation apparatus that bends the bending portion in the upward, downward, leftward, and rightward directions include one in which an upward and downward bending operation knob (hereinafter abbreviated as an upward and downward knob) and a leftward and rightward bending operation knob (hereinafter abbreviated as a leftward and rightward knob) are stacked on one side surface of an operation portion, as illustrated in Japanese Patent Application Laid-Open Publication No. 2005-245545 (hereinafter referred to as Literature 1) and one in which a finger rest portion of an upward and downward bending operation lever (hereinafter abbreviated as an upward and downward lever) and a finger rest portion of a leftward and rightward bending operation lever (hereinafter abbreviated as a leftward and rightward lever) are provided on left and right sides in an upper surface side region of an operation portion, as illustrated in Japanese Patent Application Laid-Open Publication No. 2005-160791 (hereinafter referred to as Literature 2).

In the endoscope in Literature 1, a surgeon appropriately selects the upward and downward knob or the leftward and rightward knob and rotates the knob clockwise or counterclockwise by a desired amount. With the rotation, a bending wire is directly pulled, and a bending portion bends at a desired angle in a desired direction.

In the endoscope in Literature 2, a surgeon appropriately selects the finger rest portion of the upward and downward lever or the finger rest portion of the leftward and rightward lever and inclines the finger rest portion in an operation portion distal end direction or an operation portion proximal end direction by a desired amount. The inclination causes a bending wire to be directly pulled and a bending portion to bend at a desired angle in a desired direction.

Note that the endoscopes in Literatures 1 and 2 are so-called manually bending endoscopes which directly pull a bending wire. An electrically bending endoscope is illustrated in, for example, Japanese Patent Application Laid-Open Publication No. 2007-222671. In the electrically bending endoscope, a surgeon tilts and operates a bending operation input unit, such as a joystick. With the operation, a bending wire is pulled by driving force of a motor, and a bending portion can be bent as instructed through the tilt of the joystick. As a result, the surgeon is liberated from direct pulling of a bending wire.

SUMMARY OF THE INVENTION

An endoscope according to one aspect of the present invention has a bending portion operation apparatus at an operation portion, the bending portion operation apparatus being for bending and operating a bending portion provided at an insertion portion, and the bending portion operation apparatus includes a dial for bending operation which is pivotable about a shaft and bends the bending portion by pivoting, a portion of the dial for bending operation provided at the operation portion being protruded at a position where the dial for bending operation is operated with a thumb of one hand grasping the operation portion, and an auxiliary dial for bending operation which has a meshing portion meshing with an outer circumferential face of the dial for bending operation and a protruding portion protruding at a position where the auxiliary dial for bending operation is operable with a finger other than the thumb of the one hand, an operation input entered at the protruding portion with the finger other than the thumb being transmitted to the bending operation dial via the meshing portion.

DETAILED DESCRIPTION OF THE PREFERRED EMBODIMENT

An embodiment of the present invention will be described below with reference to the drawings.

Figure 1:
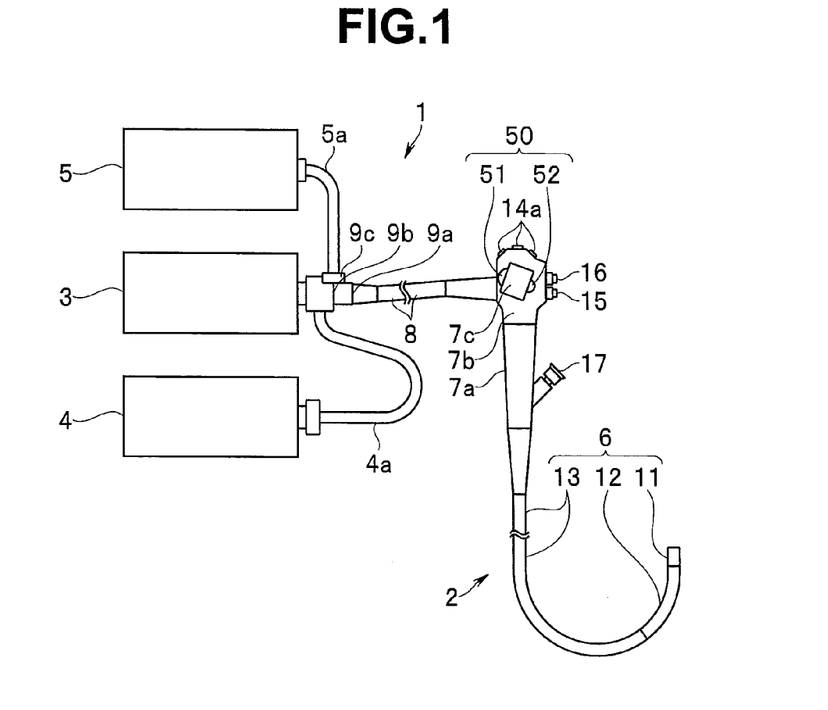
FIG. 1 is a view for explaining an electrically bending endoscope apparatus.

As shown in FIG. 1, an electrically bending endoscope apparatus 1 includes an electrically bending endoscope (hereinafter abbreviated as an endoscope) 2, a light source apparatus 3, a video processor 4, and a bending control apparatus 5. The endoscope 2 has a bending drive portion. The light source apparatus 3 supplies illuminating light to the endoscope 2. The video processor 4 performs signal processing for image pickup means which is incorporated in the endoscope 2. The bending control apparatus 5 controls driving by the bending drive portion of the endoscope 2.

The endoscope 2 includes an insertion portion 6 and an operation portion 7. The operation portion 7 is provided on a proximal end side of the insertion portion 6 to be continuous with the insertion portion 6 and doubles as a grasping portion. A flexible universal cord 8 extends from a side portion of the operation portion 7. A light guide connector 9a is provided at an end portion of the universal cord 8 toward the light source apparatus 3. The light guide connector 9a is detachably connected to the light source apparatus 3.

A video connector 9b and an angle connector 9c are provided at a side portion of the light guide connector 9a. One end of a first connecting cable 4a is detachably connected to the video connector 9b. The other end is connected to the video processor 4. One end of a second connecting cable 5a is detachably connected to the angle connector 9c. The other end is connected to the bending control apparatus 5.

The insertion portion 6 is composed of a rigid distal end portion 11, a bendable bending portion 12, and an elongated flexible tube portion 13 having flexibility which are provided in an order starting from a distal end side to be continuous with one another.

The operation portion 7 includes a grasping portion 7a, an operation portion body 7b, and a dial disposition portion 7c. The grasping portion 7a is a site to be grasped by, for example, a surgeon. A plurality of video switches 14a, an air/water feeding button 15, a suction button 16, and the like are provided at the operation portion body 7b, in addition to the dial disposition portion 7c.

Note that reference numeral 17 denotes a treatment instrument insertion port. A treatment instrument, such as biopsy forceps, is guided into a body via the treatment instrument insertion port 17.

The dial disposition portion 7c is provided at a predetermined position of the operation portion body 7b. A bending portion operation apparatus 50 for bending and operating the bending portion 12 is provided at the dial disposition portion 7c. The bending portion operation apparatus 50 includes dials 51 for bending operation and auxiliary dials 52 for bending operation. The dials 51 for bending operation are bending operation input units.

In the present embodiment, diameters of the auxiliary dials 52 for bending operation are set to be smaller than diameters of the dials 51 for bending operation. A portion of each dial 51 for bending operation protrudes from one surface of the dial disposition portion 7c. In contrast, a portion of each auxiliary dial 52 for bending operation protrudes from the other surface facing the one surface.

Figure 2:
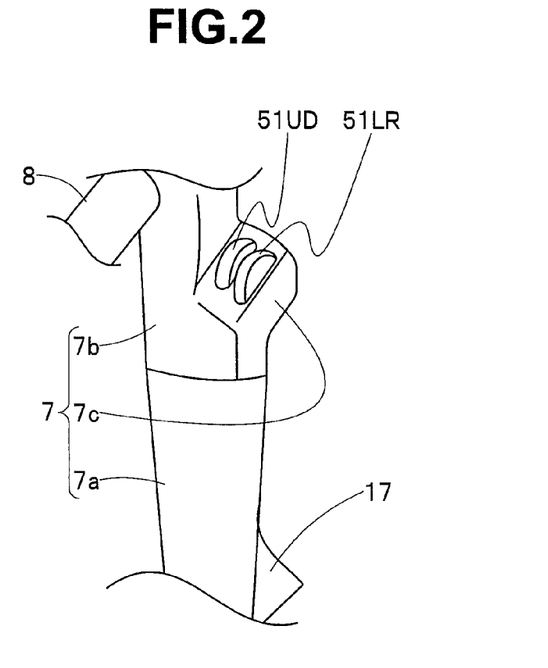
FIG. 2 is a view showing a dial for upward and downward bending operation and a dial for leftward and rightward bending operation which are provided at a dial disposition portion.

As shown in FIG. 2, a part of a dial 51UD for upward and downward bending operation and a part of a dial 51LR for leftward and rightward bending operation protrude from the one surface of the dial disposition portion 7c. The dial 51UD for upward and downward bending operation and the dial 51LR for leftward and rightward bending operation are placed parallel to each other.

Although not shown, a portion of an auxiliary dial 52UD for upward and downward bending operation and a portion of an auxiliary dial 52LR for leftward and rightward bending operation protrude on the other surface side and are placed parallel to each other.

The one surface and the other surface of the dial disposition portion 7c are formed to be inclined at a predetermined angle relative to a longitudinal axis of the operation portion 7. The angle is set in consideration of ease of operation of the dial 51UD for upward and downward bending operation and dial 51LR for leftward and rightward bending operation and ease of operation of the auxiliary dial 52UD for upward and downward bending operation and auxiliary dial 52LR for leftward and rightward bending operation.

In the present embodiment, the dial 51UD for upward and downward bending operation and the dial 51LR for leftward and rightward bending operation are arranged so as to be suitable for operation with a thumb of a hand grasping the operation portion 7, as will be described later. In contrast, the auxiliary dial 52UD for upward and downward bending operation and the auxiliary dial 52LR for leftward and rightward bending operation are arranged so as to be suitable for operation with a finger, such as a middle finger or a ring finger, other than the thumb of the hand grasping the operation portion 7.

Figure 3:
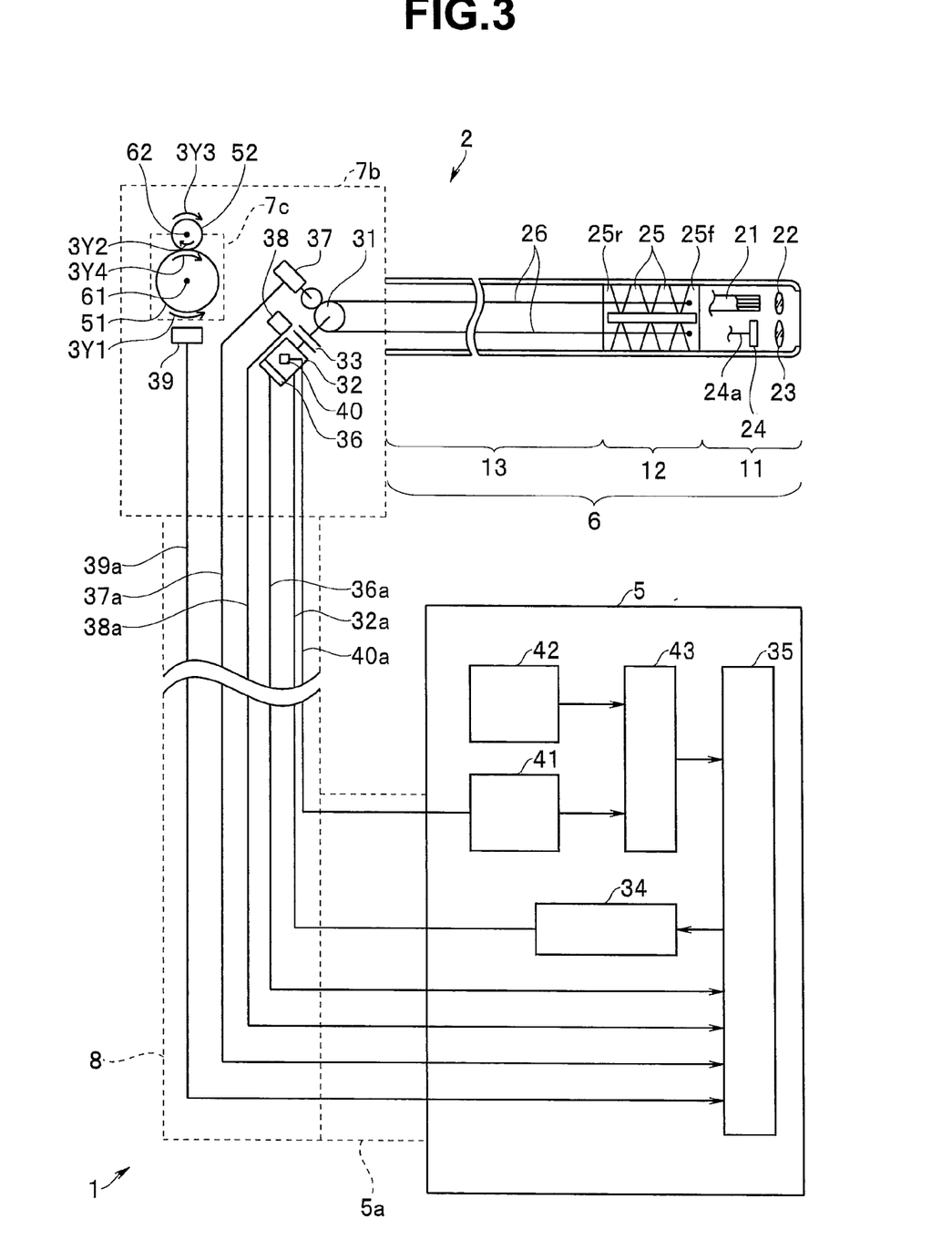
FIG. 3 is a view for explaining a relationship between an electrically bending endoscope and a bending control apparatus.

As shown in FIG. 3, a light guide 21 is inserted in and extends through the insertion portion 6. An illumination optical system 22 is provided at a distal end face of the light guide 21. Reference numeral 23 denotes an objective optical system; and 24, an image pickup apparatus as the image pickup means. The image pickup apparatus 24 includes an image pickup device, such as a CCD. An electric signal obtained through photoelectric conversion by the image pickup apparatus 24 is outputted to the video processor 4 via a signal cable 24a.

The bending portion 12 is, for example, configured to bend in upward, downward, leftward, and rightward directions by coupling a plurality of bending pieces 25, 25, . . . such that adjacent ones of the bending pieces are pivotable relative to each other. A most distal end bending piece 25f constituting the bending portion 12 is connected to a proximal end side of the distal end portion 11. A most proximal end bending piece 25r is connected to a distal end side of the flexible tube portion 13.

Reference numeral 26 denotes a bending wire for bending the bending portion 12. In the present embodiment, the bending wires 26 bend the bending portion 12 in upward and downward directions or leftward and rightward directions of an observation field of view. The bending wires 26 are arranged inside the insertion portion 6. Respective distal ends of the bending wires 26 are fixed to positions corresponding to the upward, downward, leftward, and rightward directions of the most distal end bending piece 25f by brazing or the like. Respective proximal ends of the bending wires 26 are fixed to, for example, a sprocket 31.

In the present embodiment, the individual bending wires 26 are configured to bend the bending portion 12 by being pulled and relaxed by driving force of a motor 32. The motor 32 is driven in accordance with rotation instructions from the dials 51 and 52.

A bending drive portion 30 is provided inside the operation portion body 7b. The bending drive portion 30 includes the sprocket 31, the motor 32, a clutch 33, an encoder 36, and a potentiometer 37.

The motor 32 rotates the sprocket 31 clockwise or counterclockwise. The sprocket 31 converts rotational motion of the motor 32 to advancing and retracting motion of the bending wires 26. That is, the sprocket 31 is pivoted to pull the bending wire 26 on one side and places the bending wire 26 on the other side in a relaxed state.

As a result, the bending portion 12 is bent in a direction corresponding to the pulled bending wire. The clutch 33 is provided between the sprocket 31 and the motor 32. The clutch 33 can switch from a state in which the clutch 33 transmits driving force of the motor 32 to, e.g., a state in which the clutch 33 disconnects the driving force, as needed. The encoder 36 detects a rotational position of the motor 32. The potentiometer 37 detects a rotational position of the sprocket 31.

Reference character 32a denotes a first signal wire which extends from the motor 32. The first signal wire 32a runs through the universal cord 8 and leads to the bending control apparatus 5 via the second connecting cable 5a. The first signal wire 32a supplies a motor driving signal from a motor amplifier 34 to the motor 32. The motor amplifier 34 is connected to a control section 35. The motor amplifier 34 is driven and controlled by the control section 35.

Reference character 36a denotes a second signal wire which extends from the encoder 36. The second signal wire 36a leads to the bending control apparatus 5 similarly to above. The second signal wire 36a transfers a first rotational position signal indicating the rotational position of the motor 32 that is detected by the encoder 36 to the control section 35.

Reference character 37a denotes a third signal wire which extends from the potentiometer 37. The third signal wire 37a leads to the bending control apparatus 5 similarly to above. The third signal wire 37a transfers a second rotational position signal indicating the rotational position of the sprocket 31 that is detected by the potentiometer 37 to the control section 35.

Reference numeral 38 denotes a clutch actuation detection switch 38. The clutch actuation detection switch 38 detects whether the clutch 33 is on or off. Reference character 38a denotes a fourth signal wire which extends from the clutch actuation detection switch 38. The fourth signal wire 38a leads to the bending control apparatus 5 similarly to above. The fourth signal wire 38a transfers a clutch actuation signal which is detected by the clutch actuation detection switch 38 to the control section 35.

The dial 51 for bending operation provided at the dial disposition portion 7c is configured to be rotatable clockwise or counterclockwise about an operation shaft 61. The auxiliary dial 52 for bending operation is configured to be rotatable clockwise or counterclockwise about an auxiliary shaft 62. The operation shaft 61 and auxiliary shaft 62 confront each other. In other words, the operation shaft 61 and auxiliary shaft 62 are arranged with a parallel positional relationship.

Note that being able to rotate clockwise and rotate counterclockwise is also referred to as pivotable.

In the present embodiment, a plurality of operation-side meshing teeth 53 are formed on an outer circumferential face of the dial 51 for bending operation. The plurality of operation-side meshing teeth 53 serve as a first meshing portion and are formed with a predetermined pitch. A plurality of auxiliary-side meshing teeth 54 are formed on an outer circumferential face of the auxiliary dial 52 for bending operation. The plurality of auxiliary-side meshing teeth 54 serve as a second meshing portion and are formed with a predetermined pitch so as to mesh with the plurality of operation-side meshing teeth 53. The operation-side meshing teeth 53 of the dial 51 for bending operation and the auxiliary-side meshing teeth 54 of the auxiliary dial 52 for bending operation are disposed in a meshed state.

Accordingly, for example, when a surgeon rotates the dial 51 for bending operation in a direction of an arrow 3Y1, the auxiliary dial 52 for bending operation rotates in a direction of an arrow 3Y2 while following the rotation. For example, when the surgeon rotates the auxiliary dial 52 for bending operation in a direction of an arrow 3Y3, the dial 51 for bending operation rotates in a direction of an arrow 3Y4 while following the rotation.

Rotation of the dial 51 for bending operation is detected by a bending operation amount detection sensor (hereinafter abbreviated as a sensor) 39. The sensor 39 detects a bending operation instruction signal including a rotational direction, an amount of rotation, and a rotational speed of the dial 51 for bending operation.

Reference character 39a denotes a sensor signal wire which extends from the sensor 39. The sensor signal wire 39a leads to the bending control apparatus 5 similarly to above. The sensor signal wire 39a transfers a rotational direction signal indicating the rotational direction of the dial 51 for bending operation, a rotational angle signal indicating the amount of rotation, and a speed signal indicating the rotational speed, which are detected by the sensor 39, to the control section 35.

The control section 35 performs calculation processing on the basis of the bending operation instruction signal inputted from the sensor 39, the first rotational position signal inputted from the encoder 36, and the second rotational position signal inputted from the potentiometer 37. The control section 35 controls the motor amplifier 34 on the basis of a calculation result to drive the motor 32. The control section 35 pulls and relaxes the respective bending wires 26 corresponding to the bending operation instruction signal and causes the bending portion 12 to operate to bend.

Note that the bending wires 26, the bending drive portion 30, the dial 51 for bending operation, the auxiliary dial 52 for bending operation, and the like for only one of the upward and downward directions and the leftward and rightward directions are depicted in FIG. 3 and that the components for the other are omitted.

The bending portion operation apparatus 50 of the electrically bending endoscope 2 configured such that the bending portion 12 bends in the upward and downward directions and the leftward and rightward directions will be described.

Figure 4A:
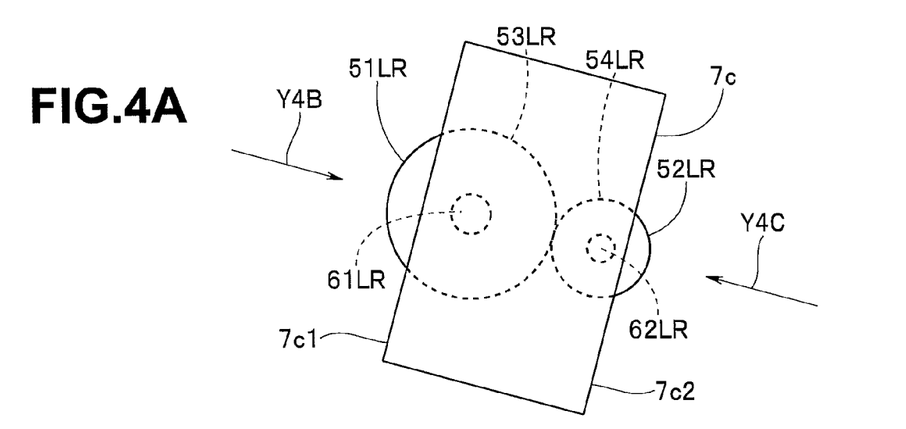
FIG. 4A is a schematic view for explaining a relationship between the dial for bending operation and an auxiliary dial for bending operation which are provided at the dial disposition portion.
Figure 4B:
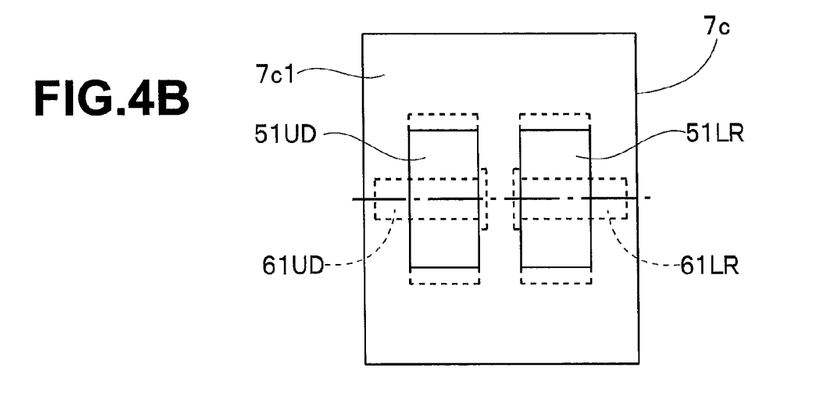
FIG. 4B is a view of the bending portion operation apparatus in FIG. 4A, as seen from a direction of an arrow Y4B.
Figure 4C:
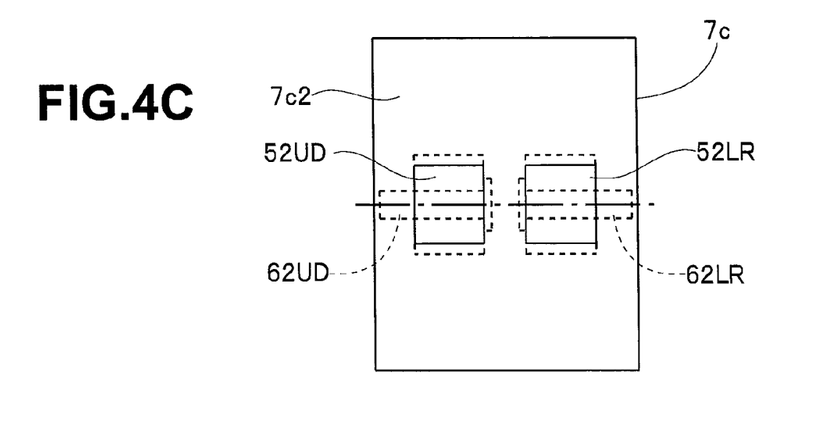
FIG. 4C is a view of the bending portion operation apparatus in FIG. 4A, as seen from a direction of an arrow Y4C.

As shown in FIGS. 4A to 4C, the bending portion operation apparatus 50 includes the dial 51UD for upward and downward bending operation and dial 51LR for leftward and rightward bending operation and the auxiliary dial 52UD for upward and downward bending operation and auxiliary dial 52LR for leftward and rightward bending operation. In the present embodiment, the dial 51UD for upward and downward bending operation and the dial 51LR for leftward and rightward bending operation have identical shapes, and the auxiliary dial 52UD for upward and downward bending operation and the auxiliary dial 52LR for leftward and rightward bending operation have identical shapes.

The dial 51UD for upward and downward bending operation is configured to be pivotable clockwise or counterclockwise about an upward and downward operation shaft 61UD serving as a first shaft. The dial 51LR for leftward and rightward bending operation is configured to be pivotable clockwise or counterclockwise about a leftward and rightward operation shaft 61LR serving as a second shaft. As shown in FIG. 4B, the upward and downward operation shaft 61UD and leftward and rightward operation shaft 61LR are arranged on an identical axis.

The auxiliary dial 52UD for upward and downward bending operation is configured to be pivotable clockwise or counterclockwise about an upward and downward auxiliary shaft 62UD serving as a third shaft. The auxiliary dial 52LR for leftward and rightward bending operation is configured to be pivotable clockwise or counterclockwise about a leftward and rightward auxiliary shaft 62LR serving as a fourth shaft. As shown in FIG. 4C, the upward and downward auxiliary shaft 62UD and leftward and rightward auxiliary shaft 62LR are arranged on an identical axis.

As shown in FIG. 4A, the leftward and rightward operation shaft 61LR and the leftward and rightward auxiliary shaft 62LR are arranged with a positional relationship such that the shafts confront each other. Although not shown in FIG. 4A, the upward and downward operation shaft 61UD and the upward and downward auxiliary shaft 62UD are arranged with a positional relationship such that the shafts confront each other.

As shown in FIG. 4B, the portion of the dial 51UD for upward and downward bending operation protrudes from one surface 7c1 of the dial disposition portion 7c. As shown in FIG. 4C, the portion of the auxiliary dial 52UD for upward and downward bending operation protrudes from the other surface 7c2.

As shown in FIGS. 4A and 4B, the portion of the dial 51LR for leftward and rightward bending operation protrudes from the one surface 7c1 of the dial disposition portion 7c. As shown in FIG. 4C, the portion of the auxiliary dial 52LR for leftward and rightward bending operation protrudes from the other surface 7c2.

Additionally, as shown in FIG. 4A, the operation-side meshing teeth 53 of the dial 51LR for leftward and rightward bending operation and the auxiliary-side meshing teeth 54 of the auxiliary dial 52LR for leftward and rightward bending operation are in a meshed state. Although not shown in FIG. 4A, the operation-side meshing teeth 53 of the dial 51UD for upward and downward bending operation and the auxiliary-side meshing teeth 54 of the auxiliary dial 52UD for upward and downward bending operation are in a meshed state.

With the configuration, the auxiliary dial 52UD for upward and downward bending operation rotates with rotation of the dial 51UD for upward and downward bending operation, and the dial 51UD for upward and downward bending operation rotates with rotation of the auxiliary dial 52UD for upward and downward bending operation. Also, the auxiliary dial 52LR for leftward and rightward bending operation rotates with rotation of the dial 51LR for leftward and rightward bending operation, and the dial 51LR for leftward and rightward bending operation rotates with rotation of the auxiliary dial 52LR for leftward and rightward bending operation.

Action of the endoscope 2 with the above-described configuration will be described.

Figure 5:
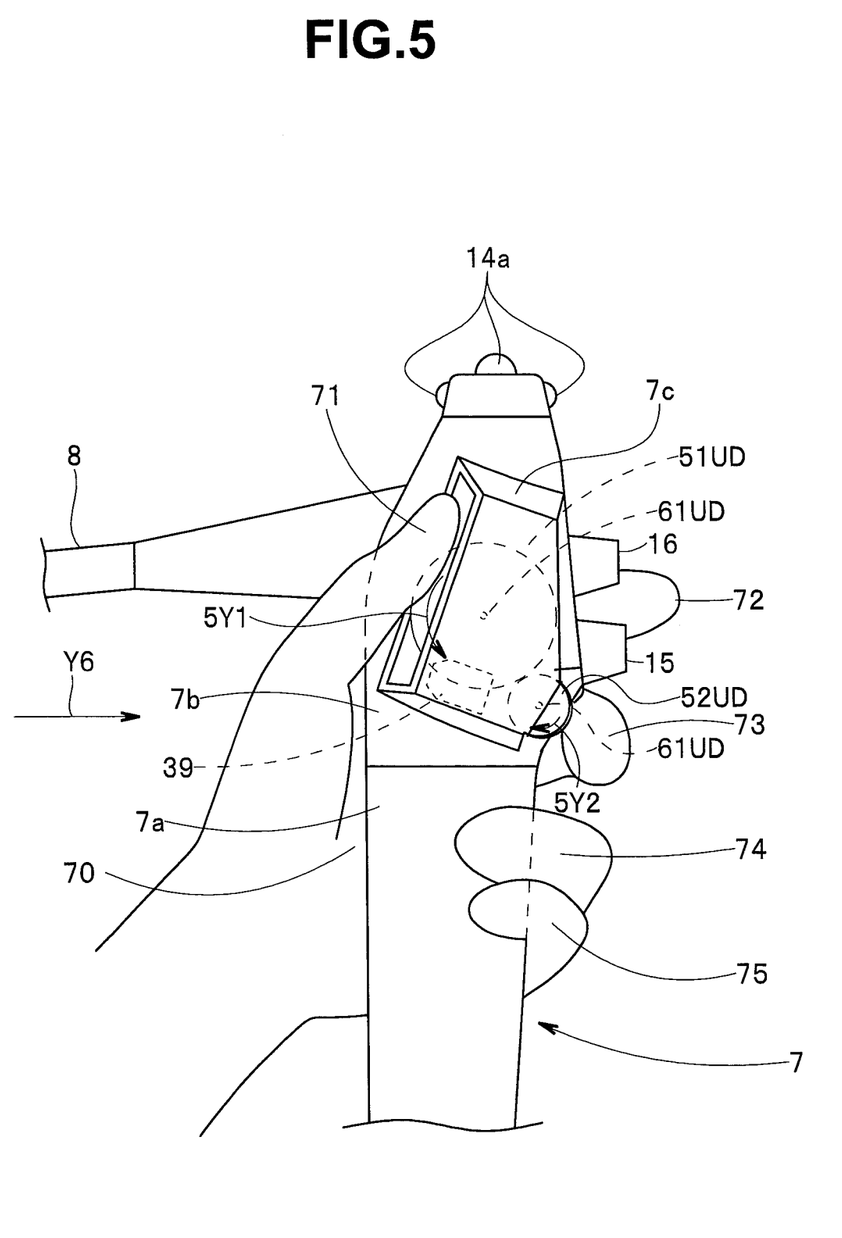
FIG. 5 is a view for explaining a state in which a surgeon grasps an operation portion with a left hand.
Figure 6:
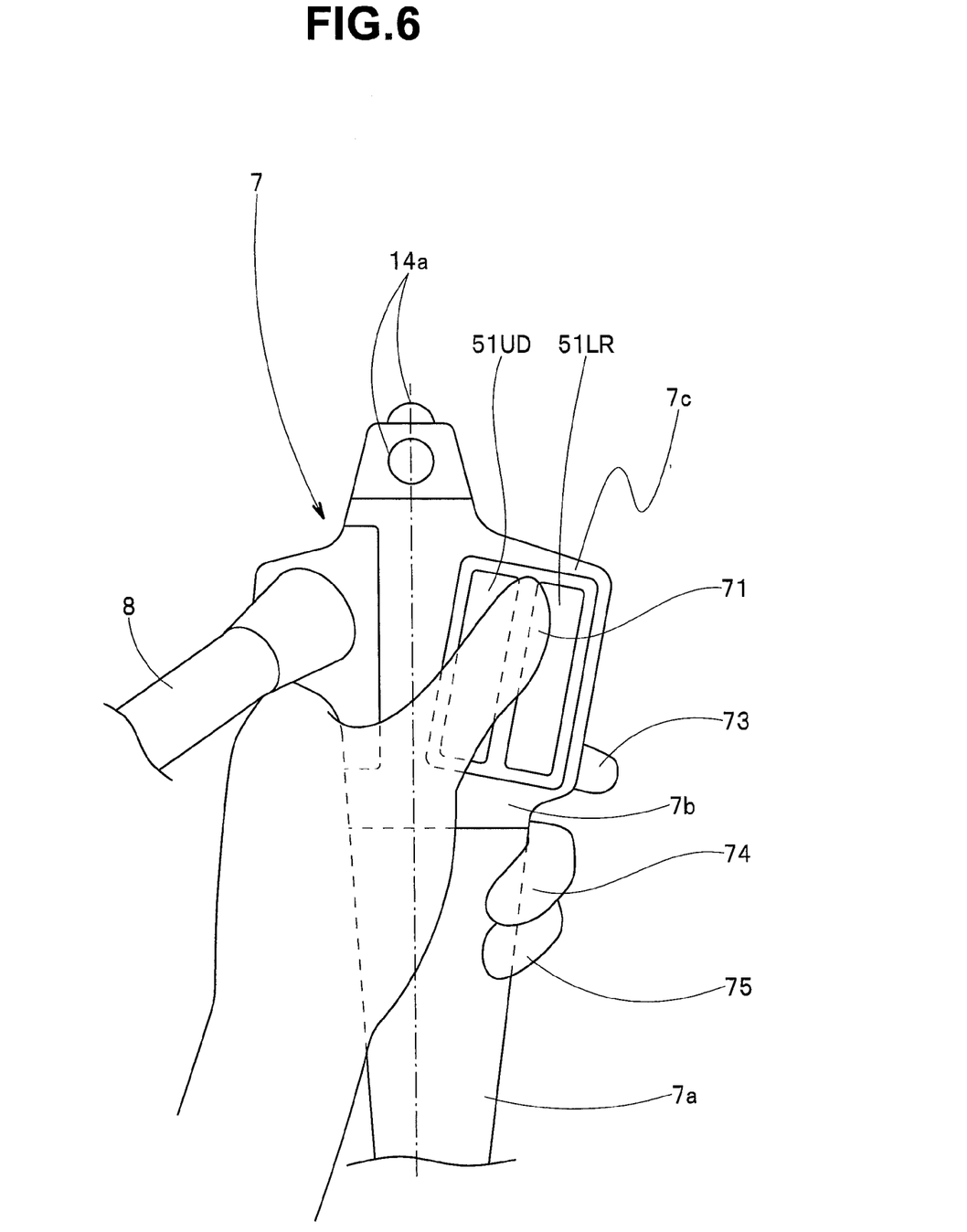
FIG. 6 is a view of the operation portion grasped by the surgeon with the left hand, as seen from a direction of an arrow Y6 in FIG. 5.

When a surgeon observes by using the endoscope 2, the surgeon grasps the grasping portion 7a of the operation portion 7 of the endoscope 2 with a left hand and grasps the insertion portion 6 with a right hand. At the time, the grasping portion 7a is grasped with a palm 70, a ring finger 74, a little finger 75, and the like of the left hand, as shown in FIGS. 5 and 6.

A thumb 71 of the left hand of the surgeon is arranged on the one surface 7c1 of the dial disposition portion 7c, on the dial 51UD for upward and downward bending operation protrudes from the one surface 7c1, or on the dial 51LR for leftward and rightward bending operation. A forefinger 72 of the left hand of the surgeon is arranged, for example, in a neighborhood of the air/water feeding button 15 or in a neighborhood of the suction button 16. A middle finger 73 of the left hand of the surgeon is arranged, for example, in a neighborhood of the auxiliary dial 52UD for upward and downward bending operation or in a neighborhood of the auxiliary dial 52LR for leftward and rightward bending operation.

When the bending portion 12 is to be bent in, for example, the upward direction, the surgeon rotates and operates the dial 51UD for upward and downward bending operation through operation with the thumb. More specifically, the surgeon rotates the dial 51UD for upward and downward bending operation counterclockwise about the upward and downward operation shaft 61UD by a desired amount, as indicated by an arrow 5Y1 in FIG. 5. At the time, the surgeon separates the middle finger 73 of the left hand from the auxiliary dial 52UD for upward and downward bending operation such that the middle finger 73 does not touch an outer circumferential face or the like of the auxiliary dial 52UD for upward and downward bending operation.

The separation allows smooth rotation of the dial 51UD for upward and downward bending operation. As a result, the motor 32 is driven under control of the control section 35, as described above, the bending wires 26 are respectively pulled and relaxed, and the bending portion 12 bends in the upward direction.

Note that the dial 51LR for leftward and rightward bending operation and the auxiliary dial 52LR for leftward and rightward bending operation are not shown in FIG. 5.

If the surgeon wants to hold a bent status and observe during bending operation of the bending portion, the surgeon stops rotational operation of the dial 51UD for upward and downward bending operation, arranges the middle finger 73 of the left hand on the outer circumferential face of the auxiliary dial 52UD for upward and downward bending operation, and presses the auxiliary dial 52UD for upward and downward bending operation with a predetermined amount of force. The auxiliary dial 52UD for upward and downward bending operation is held by the middle finger 73 of the left hand. As a result, a rotational position of the dial 51UD for upward and downward bending operation is maintained, and the bent status of the bending portion 12 is held.

If the surgeon wants to change the bent status of the bending portion 12 by a slight amount at a time, the surgeon operates the auxiliary dial 52UD for upward and downward bending operation. That is, the surgeon rotates and operates the auxiliary dial 52UD for upward and downward bending operation with the middle finger 73 of the left hand. At the time, the surgeon rotates the auxiliary dial 52UD for upward and downward bending operation, for example, clockwise about the upward and downward auxiliary shaft 62UD through operation with the middle finger 73, as indicated by an arrow 5Y2. The dial 51UD for upward and downward bending operation is rotated counterclockwise by a slight amount at a time with the clockwise rotation of the auxiliary dial 52UD for upward and downward bending operation. As a result, the bending portion 12 bends gradually in the upward direction.

As described above, the bending portion operation apparatus 50 is provided with the dial 51UD for upward and downward bending operation and auxiliary dial 52UD for upward and downward bending operation and the dial 51LR for leftward and rightward bending operation and auxiliary dial 52LR for leftward and rightward bending operation, the dial 51UD for upward and downward bending operation and the auxiliary dial 52UD for upward and downward bending operation are placed in a meshed state, and the dial 51LR for leftward and rightward bending operation and the auxiliary dial 52LR for leftward and rightward bending operation are placed in a meshed state.

As a result, the surgeon can bend the bending portion 12 in a desired one of the upward, downward, leftward, and rightward directions by performing an operation of appropriately rotating any one of the dials 51UD and 51LR for bending operation and the auxiliary dials 52UD and 52LR for bending operation.

Diameters of the auxiliary dials 52UD and 52LR for bending operation are set to be smaller than diameters of the dials 51UD and 51LR for bending operation to allow rotational operation with a small amount of force. Additionally, rotational operation of the auxiliary dials 52UD and 52LR for bending operation allows fine adjustment operation that changes the bent status of the bending portion 12 by a slighter amount at a time than rotational operation of the dials 51UD and 51LR for bending operation.

The surgeon can fix and maintain a rotational position of the dial 51UD (or 51LR) for bending operation by pressing and holding the corresponding auxiliary dial 52UD (or 52LR) for bending operation, during operation of the dial 51UD (or 51LR) for bending operation.

As a result, the surgeon can easily hold the bent status of the bending portion 12 without a need to operate a lever for regulating rotation of a knob which is provided in a conventional manually bending endoscope with a knob.

Note that the upward and downward operation shaft 61UD and the leftward and rightward operation shaft 61LR are arranged on the identical axis in the above-described embodiment. However, the upward and downward operation shaft 61UD and the leftward and rightward operation shaft 61LR may be constructed as one integrated operation shaft, instead of arranging the upward and downward operation shaft 61UD and leftward and rightward operation shaft 61LR on the identical axis. Similarly, the upward and downward auxiliary shaft 62UD and the leftward and rightward auxiliary shaft 62LR may be constructed as an integrated operation shaft.

In the above-described embodiment, the dial 51UD for upward and downward bending operation and the dial 51LR for leftward and rightward bending operation are made to have the identical shapes, and the auxiliary dial 52UD for upward and downward bending operation and the auxiliary dial 52LR for leftward and rightward bending operation are made to have the identical shapes. However, the dial 51UD for upward and downward bending operation and the dial 51LR for leftward and rightward bending operation may be made to have different shapes, and the auxiliary dial 52UD for upward and downward bending operation and the auxiliary dial 52LR for leftward and rightward bending operation may be made to have different shapes.

Figure 7A:
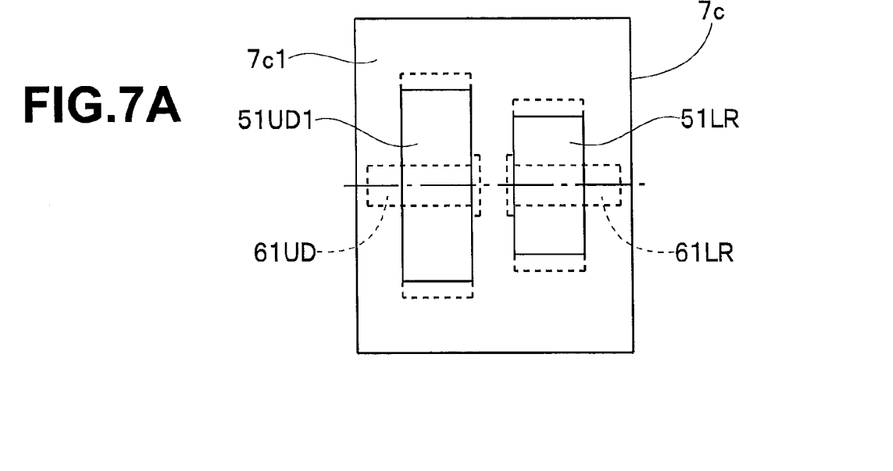
FIG. 7A is a schematic view showing a configuration example in which a dial for upward and downward bending operation having a different diameter is disposed at the dial disposition portion.
Figure 7B:
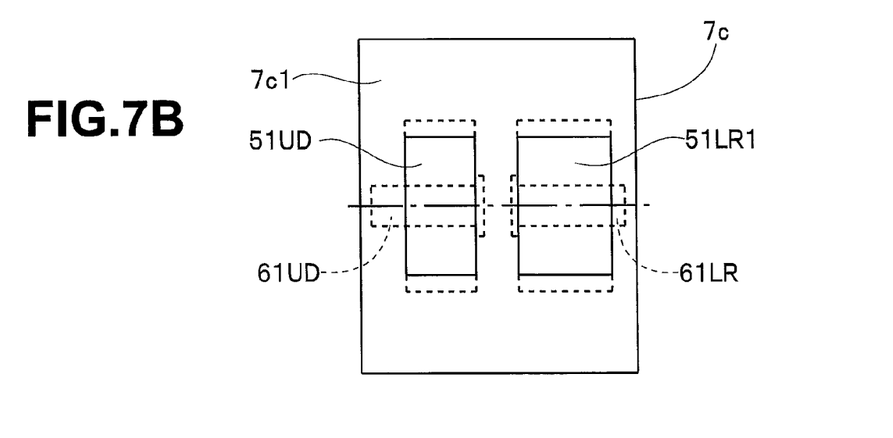
FIG. 7B is a schematic view showing a configuration example in which a dial for leftward and rightward bending operation having a different width is disposed at the dial disposition portion.

More specifically, as shown in FIG. 7A, a diameter of a dial 51UD1 for upward and downward bending operation is set to be larger or smaller than the diameter of the dial 51LR for leftward and rightward bending operation. Alternatively, as shown in FIG. 7B, a width of a dial 51LR1 for leftward and rightward bending operation is set to be larger or smaller than a width of the dial 51UD for upward and downward bending operation.

In addition, the diameter of the auxiliary dial 52UD for upward and downward bending operation and the diameter of the auxiliary dial 52LR for leftward and rightward bending operation are set to be different or a width of the auxiliary dial 52UD for upward and downward bending operation and a width of the auxiliary dial 52LR for leftward and rightward bending operation are set to be different.

Figure 7C:
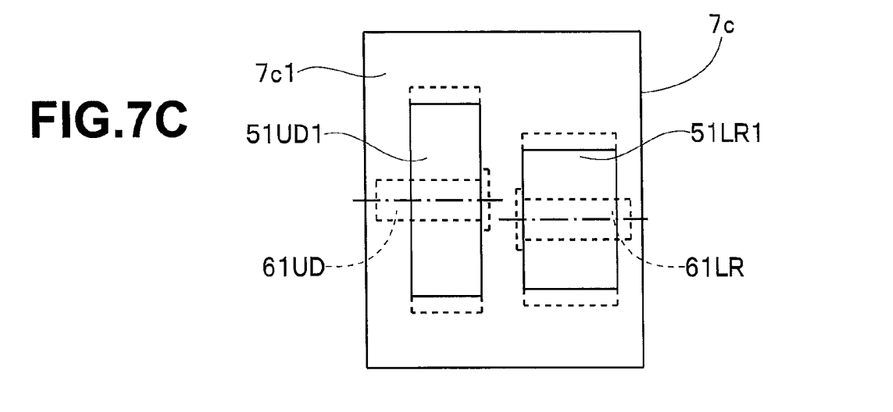
FIG. 7C is a schematic view showing a configuration example in which the dial for upward and downward bending operation having the different diameter and the dial for leftward and rightward bending operation having the different width are disposed around respective operation shafts which are positionally shifted parallel to each other.

In the above-described embodiment, the upward and downward operation shaft 61UD and the leftward and rightward operation shaft 61LR are arranged on the identical axis, and the upward and downward auxiliary shaft 62UD and the leftward and rightward auxiliary shaft 62LR are arranged on the identical axis. However, the upward and downward operation shaft 61UD and the leftward and rightward operation shaft 61LR may be positionally shifted from each other with a parallel positional relationship, as shown in FIG. 7C. Although not shown in FIG. 7C, the upward and downward auxiliary shaft 62UD and the leftward and rightward auxiliary shaft 62LR may be positionally shifted from each other with a parallel positional relationship.

Note that, in FIG. 7C, the dial 51UD1 for upward and downward bending operation is provided around the upward and downward operation shaft 61UD, and the dial 51LR1 for leftward and rightward bending operation is provided around the leftward and rightward operation shaft 61LR.

In the above-described embodiment, the operation-side meshing teeth 53 of the dial 51UD (or 51LR) for bending operation and the auxiliary-side meshing teeth 54 of the auxiliary dial 52UD (or 52LR) for bending operation are made to mesh directly with each other.

Figure 8A:
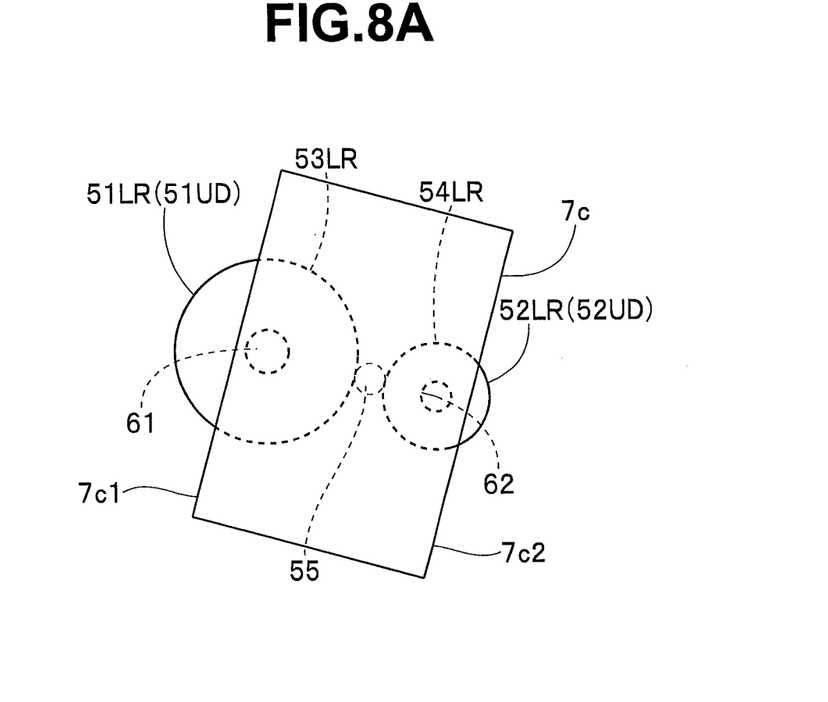
FIG. 8A is a schematic view for explaining a configuration in which operation-side meshing teeth formed on an outer circumferential face of the dial for bending operation and operation-side meshing teeth formed on an outer circumferential face of the auxiliary dial for bending operation are made to mesh with an idle gear between the sets of teeth.

However, an idle gear (idler gear) 55 may be made to mesh with the operation-side meshing teeth 53 and auxiliary-side meshing teeth 54 between the operation-side meshing teeth 53 and the auxiliary-side meshing teeth 54 to transmit rotation of the dial 51UD (or 51LR) for bending operation to the auxiliary dial 52UD (or 52LR) for bending operation or to transmit rotation of the auxiliary dial 52UD (or 52LR) for bending operation to the dial 51UD (or 51LR) for bending operation, as shown in FIG. 8A.

Note that a rotational direction of the dial 51UD (or 51LR) for bending operation is made different from a rotational direction of the auxiliary dial 52UD (or 52LR) for bending operation by providing an odd number of idle gears 55. The rotational direction of the dial 51UD (or 51LR) for bending operation is made identical to the rotational direction of the auxiliary dial 52UD (or 52LR) for bending operation by providing an even number of idle gears 55, like the above-described embodiment.

Figure 8B:
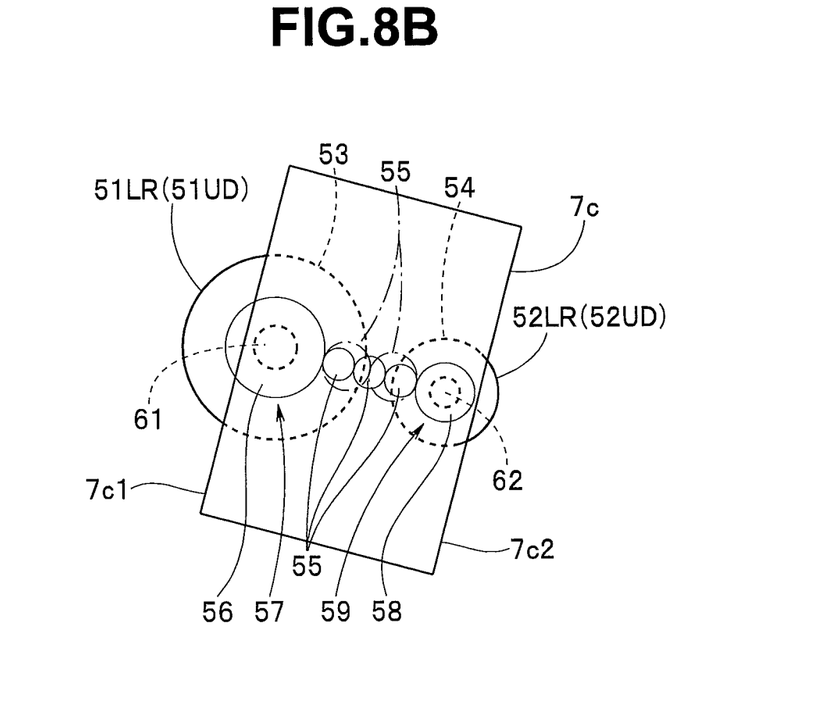
FIG. 8B is a schematic view for explaining a configuration in which operation-side meshing teeth formed on an outer circumferential face of a protruding portion provided at the dial for bending operation and operation-side meshing teeth formed on an outer circumferential face of a protruding portion provided at the auxiliary dial for bending operation are made to mesh with idle gears between the sets of teeth.

In the above-described embodiment, the operation-side meshing teeth 53 are formed on the outer circumferential face of each dial 51 for bending operation, and the auxiliary-side meshing teeth 54 are formed on the outer circumferential face of each auxiliary dial 52 for bending operation. However, as shown in FIG. 8B, an operation-side protruding portion 56 which has a diameter smaller than an outer diameter is provided on a side surface of the dial 51 for bending operation. An auxiliary-side protruding portion 58 which has a diameter smaller than an outer diameter is provided on a side surface of the auxiliary dial 52 for bending operation. Operation-side protruding portion meshing teeth 57 as a first meshing portion are formed with a predetermined pitch on an outer circumferential face of the operation-side protruding portion 56. Auxiliary-side protruding portion meshing teeth 59 as a second meshing portion meshing with the operation-side protruding portion meshing teeth 57 are formed with a predetermined pitch on an outer circumferential face of the auxiliary-side protruding portion 58.

In addition, for example, three idle gears 55 indicated by solid lines or two idle gears 55 indicated by alternate long and short dashed lines are provided between the operation-side protruding portion meshing teeth 57 and the auxiliary-side protruding portion meshing teeth 59, and the operation-side protruding portion meshing teeth 57 and the auxiliary-side protruding portion meshing teeth 59 are made to mesh with the idle gears 55 between the sets of teeth.

As described above, the operation-side protruding portion meshing teeth 57 are provided on the outer circumferential face of the operation-side protruding portion 56, and the auxiliary-side protruding portion meshing teeth 59 are provided on the outer circumferential face of the auxiliary-side protruding portion 58. The operation-side protruding portion meshing teeth 57 and the auxiliary-side protruding portion meshing teeth 59 are made to mesh with the idle gears 55 between the sets of teeth. As a result, actions and effects similar to actions and effects of the configuration in FIG. 8A can be obtained, and improvement in workability can be achieved by constructing the outer circumferential face of the dial 51 for bending operation and the outer circumferential face of the auxiliary dial 52 for bending operation as dedicated finger rest portions.

Note that a belt or a chain may be provided instead of providing an idler to transmit rotation of the dial 51 for bending operation to the auxiliary dial 52 for bending operation or transmit rotation of the auxiliary dial 52 for bending operation to the dial 51 for bending operation.

Figure 9A:
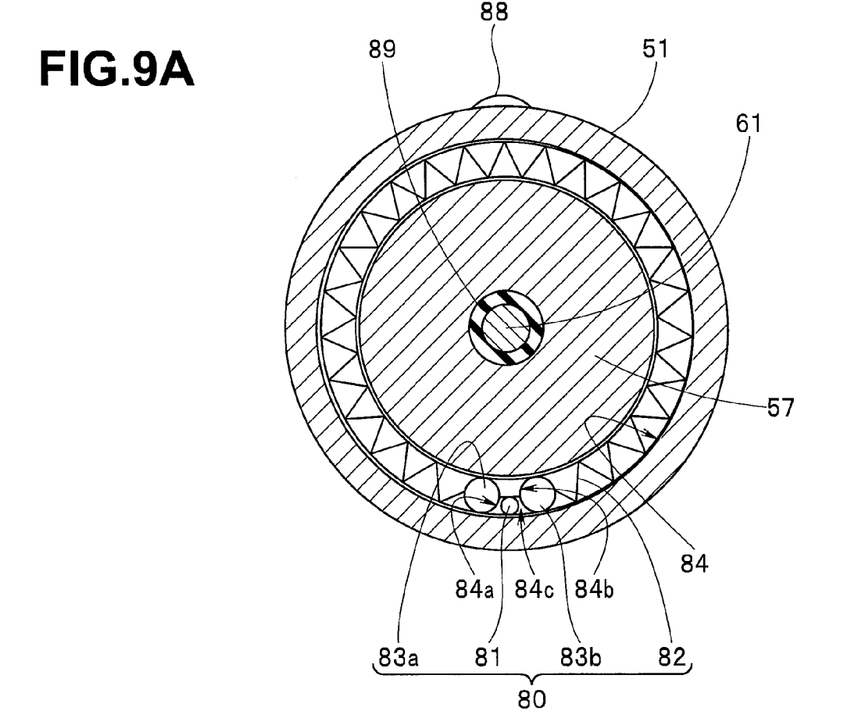
FIG. 9A is a view for explaining an origin setting/resetting mechanism.

Origin setting/resetting mechanisms are further provided at the dials 51UD and 51LR for bending operation, respectively. Each origin setting/resetting mechanism has a mechanism for arranging the dial 51UD (or 51LR) for bending operation at an origin position and a mechanism for returning the dial 51UD (or 51LR) for bending operation to the origin position after the dial 51UD (or 51LR) for bending operation is rotated and operated clockwise or counterclockwise.

As shown in FIG. 9A, an origin setting/resetting mechanism 80 includes a pin 81, a coil spring 82, and one pair of steel balls 83a and 83b. Reference numeral 88 denotes a protrusion for notification, which notifies a surgeon or the like of an initial position of the dial 51 for bending operation.

Note that the surgeon or the like may be notified of the initial position of the dial 51 for bending operation by providing a recessed portion for notification instead of the protrusion 88 for notification.

The pin 81 is provided at a predetermined position of the dial disposition portion (not shown in FIG. 9A). The first steel ball 83a is integrally fixed to one end of the coil spring 82. The second steel ball 83b is integrally fixed to the other end of the coil spring 82. A ring-shaped groove 84 is formed in one side surface of the dial 51 for bending operation.

In the ring-shaped groove 84, the pin 81, the coil spring 82, and the one pair of steel balls 83a and 83b are arranged. The ring-shaped groove 84 includes a first terminal 84a, a second terminal 84b, and a communicating groove 84c. The first terminal 84a is a surface at which the first steel ball 83a is to be arranged in contact with the surface. The second terminal 84b is a surface at which the second steel ball 83b is to be arranged in contact with the surface. The communicating groove 84c causes the first terminal 84a and the second terminal 84b to communicate with each other. The communicating groove 84c is formed to have a width larger than a diameter of the pin 81. That is, the pin 81 is configured to be capable of passing through the communicating groove 84c.

While the dial 51 for bending operation is not being rotated clockwise or counterclockwise, the steel ball 83a is arranged at the terminal 84a due to biasing force of the coil spring 82, and the steel ball 83b is arranged at the terminal 84b due to the biasing force of the coil spring 82. As a result, the dial 51 for bending operation is arranged in an initial state (origin-arranged state), as shown in FIG. 9A.

Figure 9B:
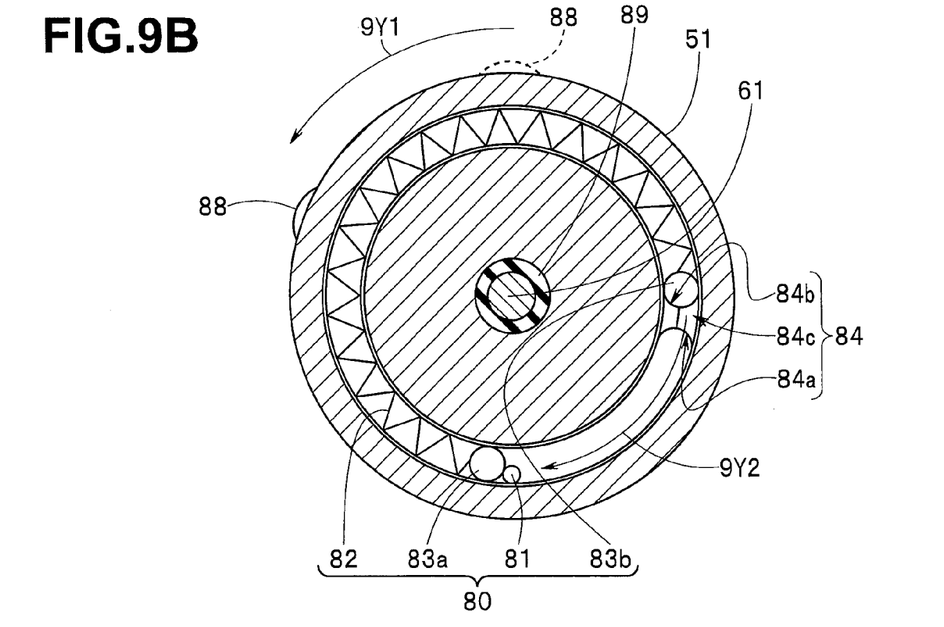
FIG. 9B is a view for explaining action of the origin setting/resetting mechanism.

When a surgeon rotates the dial 51 for bending operation, for example, in a direction of an arrow 9Y1, as shown in FIG. 9B, the first terminal 84a of the ring-shaped groove 84 is moved to pass by the pin 81 with the rotation of the dial 51 for bending operation. The first steel ball 83a then comes into contact with the pin 81 due to the biasing force of the coil spring 82. The second steel ball 83b arranged at the second terminal 84b contracts the coil spring 82 with the movement of the second terminal 84b. At the time, the surgeon rotates the dial 51 for bending operation against the biasing force of the coil spring 82.

When the surgeon releases a hand from the dial 51 for bending operation during the operation, the second steel ball 83b starts to move toward a direction of an arrow 9Y2 due to the biasing force of the coil spring 82. That is, the dial 51 for bending operation is rotated in the direction of the arrow 9Y2 and returns to the initial state.

In the present embodiment, for example, an O-ring 89 is provided between the dial 51 for bending operation and the operation shaft 61. The O-ring 89 prevents the dial 51 for bending operation from being rapidly rotated to change the bending portion 12 from a bent state to a substantially straight state when the surgeon releases the hand from the dial 51 for bending operation. In the configuration, elastic force of the coil spring 82 is set to an optimum elastic force in consideration of resistance of the O-ring 89.

As a result, the dial 51 for bending operation provided with the O-ring 89 gradually returns to the original state without returning rapidly from a rotational operation position to the initial position due to the biasing force of the coil spring 82.

Note that an electrically bending endoscope which pulls a bending wire by driving force of an electric motor is used as an endoscope in the above-described embodiment. The endoscope, however, is not limited to an electrically bending endoscope and may be a manually bending endoscope which directly pulls a bending wire through dial operation. In the above-described embodiment, the endoscope is configured such that a bending portion bends in four directions, upward and downward directions and leftward and rightward directions. The bending portion, however, is not limited to one configured to bend in the four directions, and the endoscope may be configured such that the bending portion bends in two directions, upward and downward directions. In the case, for example, the dial 51LR for leftward and rightward bending operation and the auxiliary dial 52LR for leftward and rightward bending operation are unnecessary.

Note that the present invention is not limited to only the above-described embodiment and that various modifications may be made without departing from scope of the invention.

What is claimed is:

1. An endoscope comprising:
   a bending portion which is bendable and provided at an insertion portion;
   a dial for bending operation which is rotatable for a bending operation of the bending portion, the dial for bending operation being provided to protrude from an outer surface of an operation portion which is provided on a proximal end side of the insertion portion, the dial for bending operation having a plurality of operation-side meshing teeth on an outer circumference;
   an auxiliary dial for bending operation which is rotatable for rotating the dial for bending operation, the auxiliary dial for bending operation being provided to protrude from the outer surface of the operation portion; and
   a plurality of auxiliary-side meshing teeth which are provided on an outer circumferential surface of the auxiliary dial for bending operation and transmit rotation of the auxiliary dial for bending operation to the dial for bending operation, a diameter of arrangement of the plurality of auxiliary-side meshing teeth being smaller than a diameter of arrangement of the plurality of operation-side meshing teeth of the dial for bending operation; wherein
   the bending portion is bendable in upward and downward directions and leftward and rightward directions,
   the dial for bending operation includes:
      a dial for upward and downward bending operation which is arranged on a first shaft provided at the operation portion, is rotatable clockwise and counterclockwise about the first shaft, and bends the bending portion in the upward direction or the downward direction by being rotated in one of a clockwise direction and a counterclockwise direction; and
      a dial for leftward and rightward bending operation which is arranged on a second shaft parallel to the first shaft, is rotatable clockwise and counterclockwise about the second shaft, and bends in the leftward direction or the rightward direction by being rotated in one of the clockwise direction and the counterclockwise direction; and
   the auxiliary dial for bending operation includes:
      an auxiliary dial for upward and downward bending operation which is arranged on a third shaft confronting the first shaft, is rotatable clockwise and counterclockwise about the third shaft, and bends the bending portion in the upward direction or the downward direction by being rotated in one of the clockwise direction and the counterclockwise direction; and
      an auxiliary dial for leftward and rightward bending operation which is arranged on a fourth shaft confronting the second shaft, is rotatable clockwise and counterclockwise about the fourth shaft, and bends in the leftward direction or the rightward direction by being rotated in one of the clockwise direction and the counterclockwise direction.

2. The endoscope according to claim 1, wherein the auxiliary dial for bending operation pivots about a shaft different from the shaft for the dial for bending operation, a position where the plurality of operation-side meshing teeth and the auxiliary-side meshing teeth mesh with each other is movable, and the auxiliary dial for bending operation follows the dial for bending operation to rotate when clockwise rotation or counterclockwise rotation of the dial for bending operation is transmitted.

3. The endoscope according to claim 1, wherein at least two shafts which are at least one of the first and second shafts and the third and fourth shafts are arranged on an identical axis.

4. The endoscope according to claim 3, wherein at least two shafts which are at least one of the first and second shafts and the third and fourth shafts are integrally constructed as one shaft.

5. The endoscope according to claim 1, wherein the plurality of operation-side meshing teeth and the plurality of auxiliary-side meshing teeth directly mesh with each other.

6. An endoscope comprising:
   a bending portion which is bendable and provided at an insertion portion;
   a dial for bending operation which is rotatable for a bending operation of the bending portion, the dial for bending operation being provided to protrude from an outer surface of an operation portion which is provided on a proximal end side of the insertion portion, the dial for bending operation having a plurality of operation-side meshing teeth on an outer circumference;
   an auxiliary dial for bending operation which is rotatable for rotating the dial for bending operation, the auxiliary dial for bending operation being provided to protrude from the outer surface of the operation portion; and
   a plurality of auxiliary-side meshing teeth which are provided on an outer circumferential surface of the auxiliary dial for bending operation and transmit rotation of the auxiliary dial for bending operation to the dial for bending operation, a diameter of arrangement of the plurality of auxiliary-side meshing teeth being smaller than a diameter of arrangement of the plurality of operation-side meshing teeth of the dial for bending operation;
   wherein at least one idle gear is provided between the plurality of operation-side meshing teeth and the plurality of auxiliary-side meshing teeth, and the idle gear is meshed with the plurality of operation-side meshing teeth and the plurality of auxiliary-side meshing teeth.

7. An endoscope comprising:
   a bending portion which is bendable and provided at an insertion portion;
   a dial for bending operation which is rotatable for a bending operation of the bending portion, the dial for bending operation being provided to protrude from an outer surface of an operation portion which is provided on a proximal end side of the insertion portion, the dial for bending operation having a plurality of operation-side meshing teeth on an outer circumference;
   an auxiliary dial for bending operation which is rotatable for rotating the dial for bending operation, the auxiliary dial for bending operation being provided to protrude from the outer surface of the operation portion; and a plurality of auxiliary-side meshing teeth which are provided on an outer circumferential surface of the auxiliary dial for bending operation and transmit rotation of the auxiliary dial for bending operation to the dial for bending operation, a diameter of arrangement of the plurality of auxiliary-side meshing teeth being smaller than a diameter of arrangement of the plurality of operation-side meshing teeth of the dial for bending operation; wherein the dial for bending operation includes a biasing member which regulates the dial for bending operation to an initial position, and the dial for bending operation is rotated clockwise or counterclockwise against biasing force of the biasing member.

\* \* \* \* \*